United States Patent [19]

Sirninger

[11] Patent Number: 5,140,978
[45] Date of Patent: Aug. 25, 1992

[54] DEVICE FOR RELIEVING TENSION IN HEAD SKIN

[76] Inventor: Karl H. A. Sirninger, 53 McIver St., Ferntree Gully, Victoria 3156, Australia

[21] Appl. No.: 410,994

[22] Filed: Sep. 22, 1989

[30] Foreign Application Priority Data

Feb. 26, 1988 [AU] Australia .................. P16984

[51] Int. Cl.⁵ .................................. A61H 7/00
[52] U.S. Cl. ........................... 128/44; 128/59; 128/62 R; 128/63
[58] Field of Search .......... 128/67, 44, 62 R, 63; 28/59

[56] References Cited

U.S. PATENT DOCUMENTS 3,141,459 7/1964 Orcutt .
4,506,659 3/1985 Chester .................. 128/59
4,646,728 3/1987 Takeda .

FOREIGN PATENT DOCUMENTS 403006 2/1923 Denmark .
266472 5/1988 European Pat. Off. .
1541303 2/1970 Fed. Rep. of Germany .
2948059 7/1981 Fed. Rep. of Germany .
755689 11/1933 France .
207417 12/1939 Switzerland .
227507 1/1925 United Kingdom .

Primary Examiner—V. Millin
Attorney, Agent, or Firm—Hovey, Williams, Timmons & Collins

[57] ABSTRACT

A device (1) for wearing on a human head to relieve tension in skin covering a skull region and so promote hair growth from the skin. The device (1) includes a carrier member (2) for positioning on a human skull; and, grip means (5) on the carrier member (2) at spaced locations so that, in use of the device (1). The grip means (5) grippingly engages skin beneath the cranium region of the skull and applies an upwardly directed force causing the skin to be shifted more up onto the cranium region, thereby relieving tension within the skin covering that cranium region.

14 Claims, 1 Drawing Sheet

DEVICE FOR RELIEVING TENSION IN HEAD SKIN

BACKGROUND OF THE INVENTION

1. Field of the Invention

This invention relates generally to a device for application to a skin surface in order to promote improved blood circulation within the scalp so as to enhance the prospects of re-growth of hair from that surface. The device is applicable for promoting regrowth of scalp hair to human heads, and it will be convenient to hereinafter describe the invention in relation to that exemplary application. It should be appreciated, however, that the invention is not limited to that application.

2. Description of the Prior Art

Baldness, either total or partial, can be both a physical and psychological disadvantage to many Persons, and a large number and variety of cosmetic treatments have been developed and promoted which are aimed at removing or alleviating that disadvantage. Such treatment may involve artificial hair replacement, including the use of wigs and hair transplant operations but such replacement can be expensive and, in any event, often give a clear and obvious impression of hair having been added to the head. Thus, hair replacement may not be entirely satisfactory in alleviating any disadvantage caused by baldness.

Other treatments involve lotions which are applied to the head scalp to promote and restore natural hair growth on the human head. These lotions are said to make the head scalp supple and also nourish that scalp so as to regenerate hair growth from existing hair follicles. In general practice, however, it is believed that these lotions have had little effect on promoting hair growth and so do little to alleviate any baldness.

SUMMARY OF THE INVENTION

It is an object of the present invention to provide a device that is applied to a skin surface to promote and restore hair growth from that surface.

With that object in mind, the present invention provides a device for wearing on a human head to relieve tension in skin covering a skull region and so promote hair growth from the skin, including: a static carrier member for positioning on a human skull; and, grip means on the carrier member at spaced locations so that, in use of the device, the grip means grippingly engages skin at the cranium region of the skull and applies an upwardly directed force causing the skin to be shifted more up onto the cranium region, thereby relieving tension within the skin covering that cranium region. After a preferably extended period of wear, the skin may be sufficiently shifted whereby skin tension will be relieved.

In at least one embodiment, the carrier member is of a resilient construction. That member is then resiliently or elastically distorted upon positioning on the human skull so as to provide the force for the grip members to grippingly engage and shift the skin. After having engaged the skin as previously described and the skin has shifted, the carrier member remain static.

In one embodiment, the carrier member is a curved carrier strip for extending over the top of the cranium region of the skull. That carrier strip has opposed end regions which are positioned immediately above a wearer's ears during device use.

In this embodiment, the grip means include at least one grip member located adjacent each carrier strip end region.

In another embodiment, the carrier member is a carrier band for extending entirely laterally about the skull immediately above a wearer's ears. In this embodiment, the carrier band may be adjustable in length to accommodate skulls of various sizes. With this carrier member, the grip means includes in at least one embodiment a series of grip members provided in spaced relation along the carrier band. Each such grip member includes a body having an open ended slot through which the carrier band passes to mount the grip member on the carrier band.

In one embodiment, the grip means is movable relative to the carrier member for adjusting the location at which the grip means engage and applies force to the skin.

In at least one embodiment, the grip means includes an array of closely spaced apart projections having terminal ends which engage the skin and through which the upwardly directed force is applied, during device use. Those projections, in one embodiment are angled so as to extend in a generally upward direction at least adjacent the terminal ends, during device use. Each projection may be bent along its length so as to extend in a generally upward direction adjacent the terminal end thereof. Moreover, those projections may be short, stiff bristles having blunt terminal ends.

The following description refers to preferred embodiments of the device of the present invention. To facilitate an understanding of the invention, reference is made in the description to the accompanying drawings where the device is illustrated in preferred embodiments. It is to be understood that the device is not limited to the preferred embodiments as hereinafter described and as illustrated in the drawings.

BRIEF DESCRIPTION OF THE DRAWINGS

In the drawings (where identical reference numerals identify the same or like components).

DESCRIPTION OF THE PREFERRED EMBODIMENTS

Figure 1:
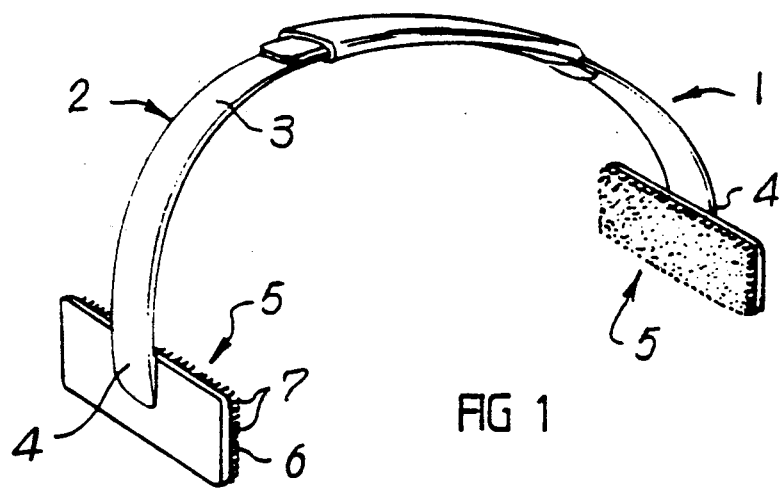
FIG. 1 is a perspective view of the device according to one preferred embodiment of the present invention.

Referring initially to FIG. 1 there is generally shown device 1. That device 1 is worn on a human head (not shown) in the manner of headphones or ear muffs, although will be located above the wearer's ears.

Device 1 includes elongate carrier member 2 in the form of carrier strip 3 having spaced end regions 4 at which grip members 5 are located. Strip 3 is curved in this embodiment to extend over the cranium region of a skull when being worn.

Carrier strip 3 may be formed in one (not shown) or more (as shown) pieces and is composed of metal or plastic or other resilient material, the material having sufficient resilient stiffness to enable grip members 5 to engage and apply an upwardly directed force to the skin. In this embodiment, during device use carrier strip 3 is distorted by pulling grip members 5 away from one another, thus resiliently stressing carrier strip 3, so that the skull can be positioned therebetween for gripping the skin at opposing locations. In use, carrier strip 3 will extend over the cranium region of the skull so that end regions 4 are located immediately above respective ears of the wearer. With this arrangement forces applied to the skull skin through grip members 5 tend to draw the skin from about the ears more up onto the cranium region. That skin is generally loose and may form into small folds or shallow creases over the cranium region.

In this embodiment, grip members 5 bear on grip areas of the skull skin, each member 5 having grip surface 6 that faces toward the skin in device use. Those surfaces may be contoured to complement the contour of the skin areas. In that regard, they may be slightly concave shaped.

Each grip member 5 is constructed so as to grippingly engage the skin against slippage. To that end, grip surfaces 6 may be roughened or otherwise provided with an anti-slip treatment (not shown). Alternatively, (as shown) grip members 5 are each provided with short projections 7. Grip members 5 with projections 7 may be particularly suitable for persons having hair in the grip areas, since projections 7 will tend to extend through that hair and press into the skin for superior grip. Projections 7 should not be so sharp at their terminal ends as to break or penetrate through the skin. Projections 7 extend in closely spaced apart arrays. Projections 7 on each grip member 5 may have a short, stiff bristle-like appearance and may be composed of metal such as stainless or surgical steel.

Grip members 5 may be rigidly connected to carrier strip 3 (as shown). Alternatively, (not shown) the connection may be through a movable joint that allows grip member movement, relative to carrier strip 3, in order to achieve proper face-to-face alignment of grip surfaces 6 with the skin grip areas. The joint may be of a swivel type.

Grip members 5 may be fixed in position on carrier strip 3 (as shown). Alternatively, (not shown) they may be movable for adjusting grip member locations. This alternative may allow device 1 to be correctly used on quite different head shapes and sizes. Adjustment may be achieved by providing grip members 5 with a connection stud (not shown) which can be fitted into a slotted hole or a selected one of a series of holes, and secured in the hole by a nut screw threaded onto the stud. Adjustment of grip member location may also be facilitated by forming carrier strip 3 of two or more pieces (as shown) which can be relatively shifted and locked together.

Grip members 5 may be of any suitable shape and size. Typically, they may provide round or elongate grip surfaces, and for example the round surfaces may be about 50 mm in diameter.

Although device 1 is shown with only two grip members 5 it should be appreciated that additional grip member numbers may be provided. In that regard, a series of grip members 5 may extend laterally from end regions 4 at least partially about the skull.

Figure 2:
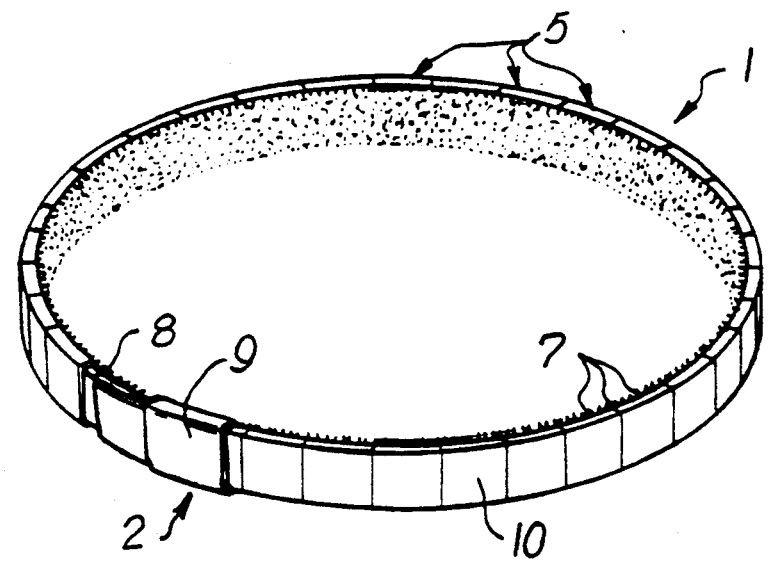
FIG. 2 is a perspective view of the device according to another preferred embodiment of the present invention; and, FIG. 3 is a perspective view of one grip member forming part of the device of FIG. 2.
Figure 3:
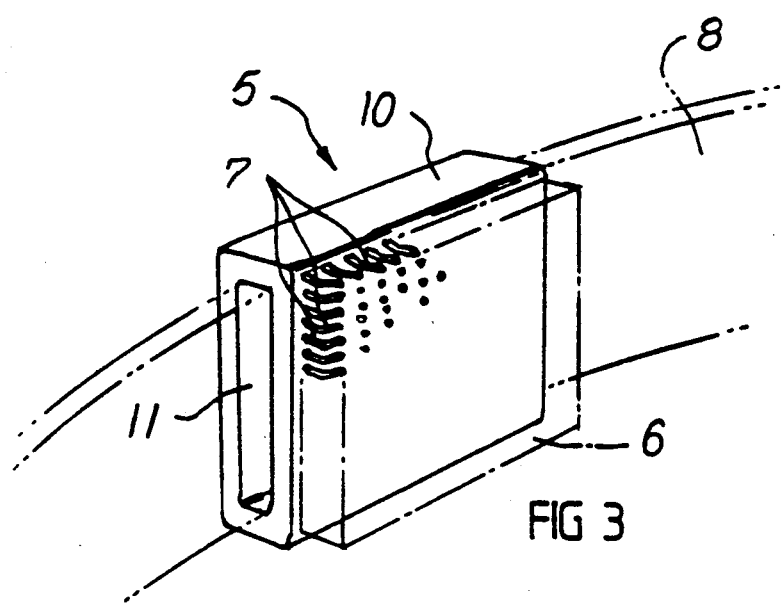

In an alternative embodiment, shown in FIGS. 2 and 3, device 1 includes elongate carrier member 2 in the form of carrier band 8 along which grip members 5 are located. Device 1 of this embodiment is worn on a human head (now shown) in the manner of a head band, carrier band 8 extending in an endless loop entirely laterally about the skull immediately above the wearer's ears.

Carrier band 8 is composed of resilient or elastic material, again so that grip members 5 engage and apply an upwardly directed force to the skin covering the skull.

In this embodiment, carrier member 2 may be of a one piece unitary construction (not shown). Alternatively, (as shown) carrier member 2 may be adjustable for device 1 to accommodate different head shapes and sizes. Adjustment may be achieved by incorporating a buckle or other connection arrangement 9 into carrier member 2, connection arrangement 9 co-acting between terminal end regions of carrier band 8 to decrease or increase the circumference of band 8.

In this embodiment, grip members 5 may extend entirely about carrier member 2 in side-by-side relation. Alternatively those members 5 may be equally or variably spaced apart entirely or partially about carrier member 2.

As in the previous embodiment each grip member 5 is constructed to grippingly engage the skin against slippage. Again, to that end grip members 5 have grip surfaces 6 roughened or otherwise provided with anti-slip treatment. One preferred grip member 5 of this embodiment is illustrated in detail in FIG. 3, and includes body 10 having a closely spaced array of short projections 7 extending therefrom to terminal ends at grip surface 6. Projections 7 are bent along their length so that they will extend in a generally upward direction toward their terminal ends engaging skull skin during device use. This angling tends to improve the upward shifting of the skin onto the cranium region.

Projections 7 as shown in FIG. 3 may also be incorporated into the device embodiment shown in FIG. 1.

Grip members 5 may be permanently fixed in position along carrier band 8 (not shown). Alternatively, (not shown) members 5 may be formed integrally with carrier band. In a further alternative (as shown) members 5 may be movable and removably fitted onto carrier band 8 to enable repositioning of member 5. To that end, body 10 is provided with open ended slot 11 through which band 8 passes. Slot 11 is shaped and sized relative to band 8 so that body 10 frictionally grips band 8 to hold member 5 in a selected position.

Body 10 is constructed of any suitable material, and by way of example may be molded from plastics material. Projections 7, again may be composed of metal such as stainless or surgical steel. Typically, grip members 5 may be square shaped and about 25×25 mm.

Although device 1 in this embodiment is shown with a series of grip members 5 positioned about carrier member 2, it should be appreciated that a single elongate grip member 5 may be substituted for two or more of those members. Thus, in one embodiment a single grip member 5 may extend entirely along carrier member 2, and may be formed integral therewith or separate therefrom.

In use, device 1 will be generally worn for periods of one or more hours, although experimentation may determine that varying the periods may be most appropriate for some persons. In any event, the device should be worn for extended periods to ensure improved blood circulation within the scalp skin so as to enhance the prospects of hair growth on the scalp.

It is to be understood that various modifications and/or alterations may be made without departing from the ambit of the present invention as defined in the claims appended hereto.

I claim:

1. A device for wearing on a human head to relieve tension in skin covering a skull region, comprising: a static carrier member for positioning on a human skull; and, grip means on the carrier member having an array of closely spaced apart short, stiff projections of bristle-like appearance with terminal ends for grippingly engaging skin at the cranium region of the skull, the carrier member applying an upwardly directed force to the skin through the projections causing the skin to be shifted more up onto the cranium region, thereby relieving tension within the skin covering that cranium region.

2. A device as claimed i claim 1, wherein the carrier member is of a resilient construction and is resiliently or elastically distorted upon positioning on the human skull thereby providing the force for the grip means to grippingly engage and shift the skin.

3. A device as claimed in claim 1, wherein the carrier member is a curved carrier strip for extending over the top of the cranium region of the skull, the carrier strip having opposed end regions positioned immediately above a wearer's ears during device use.

4. A device as claimed in claim 3, wherein the grip means includes at least one grip member located adjacent each carrier strip end region.

5. A device as claimed in claim 1, wherein the carrier member is a carrier band for extending entirely laterally about the skull immediately above a wearer's ears.

6. A device as claimed in claim 5, wherein the carrier band is adjustable in length to accommodate skulls of various sizes.

7. A device as claimed in claim 5, wherein the grip means includes a series of grip members provided in spaced relation along the carrier band.

8. A device as claimed in claim 7, wherein each grip member includes a body having an open ended slot through which the carrier band passes to mount the grip member on the carrier band.

9. A device as claimed in claim 1, wherein the grip means is movable relative to the carrier member for adjusting the location at which the grip means engage and applies force to the skin.

10. A device as claimed in claim 1, wherein the projections are angled so as to extend in a generally upward direction at least adjacent the terminal ends, during device use.

11. A device as claimed in claim 10, wherein each projection is bent along its length so as to extend in a generally upward direction adjacent the terminal end thereof.

12. A device as claimed in claim 1, wherein the projections are short, stiff bristles having blunt terminal ends.

13. A device for wearing on a human head to relieve tension in skin covering a skull region, comprising: a resiliently distortable curved carrier strip for extending over the top of the cranium region of the skull, the carrier strip having opposed end regions for positioning immediately above the wearer's ears; and, a grip member provided at each carrier strip end region and having an array of short stiff bristles with terminal ends which engage skin at the cranium region of the skull, the short stiff bristles being angled so as to extend in a generally upward direction at the terminal ends during device use, whereby in use of the device resilient distortion of the carrier strip causes the short stiff bristles to apply an upwardly directed force to the skin so that the skin is pushed more up onto the cranium region, thereby relieving tension within the skin covering that cranium region.

14. A device for wearing on a human head to relieve tension in skin covering a skull region, comprising: a resilient carrier bend for extending entirely laterally about the skull immediately above a wearer's ears; and, a series of grip members provided in spaced relation along the carrier band so as to extend at least partially therealong, each grip member having an array of short stiff bristles with terminal ends which engage skin at the cranium region of the skull, the short stiff bristles being angled so as to extend in a generally upward direction at the terminal ends during device use, whereby in use of the device resilient distortion of the carrier band causes the short stiff bristles to apply an upwardly directed force to the skin so that the skin is pushed more up onto the cranium region, thereby relieving tension within the skin covering that cranium region.

* * * * *